United States Patent
Giraud et al.

(10) Patent No.: US 9,572,744 B2
(45) Date of Patent: Feb. 21, 2017

(54) MASSAGE DEVICE WITH A MASSAGE HEAD EQUIPPED WITH MASSAGE WHEELS

(71) Applicant: SEB S.A., Ecully (FR)

(72) Inventors: Camille Giraud, Lyons (FR); Franck Mandica, Francheville (FR)

(73) Assignee: SEB S.A., Ecully (FR)

( * ) Notice: Subject to any disclaimer, the term of this patent is extended or adjusted under 35 U.S.C. 154(b) by 600 days.

(21) Appl. No.: 14/087,497

(22) Filed: Nov. 22, 2013

(65) Prior Publication Data

US 2014/0142480 A1 May 22, 2014

(30) Foreign Application Priority Data

Nov. 22, 2012 (FR) ...................................... 12 61108

(51) Int. Cl.
*A61H 15/00* (2006.01)
*A61H 7/00* (2006.01)
(Continued)

(52) U.S. Cl.
CPC .......... *A61H 15/0078* (2013.01); *A61H 7/007* (2013.01); *A61H 15/0085* (2013.01); *A61N 1/0428* (2013.01); *A61N 1/303* (2013.01); *A61H 15/02* (2013.01); *A61H 23/02* (2013.01); *A61H 2007/009* (2013.01);
(Continued)

(58) Field of Classification Search
CPC .......... A61H 7/00; A61H 7/004; A61H 7/005; A61H 7/007; A61H 7/008; A61H 15/00; A61H 15/0078; A61H 15/0085; A61H 2015/007; A61H 2015/0014; A61H 2015/0021; A61H 2015/0028; A61H 2015/0035; A61H 2015/0057

See application file for complete search history.

(56) References Cited

U.S. PATENT DOCUMENTS 2,003,272 A * 5/1935 Betz ................... A61H 15/0085
601/133
2,819,715 A * 1/1958 Calhoun ............ A61H 15/0092
601/125
(Continued)

FOREIGN PATENT DOCUMENTS

| EP | 0666071 A1 | 2/1995 |
| EP | 1973510 B1 | 9/2010 |
| FR | 2589726 A1 | 5/1987 |

*Primary Examiner* — Valerie L Woodward
(74) *Attorney, Agent, or Firm* — The Webb Law Firm

(57) ABSTRACT

A massage device includes a body which contains motor and massage head, where installation mechanism is located between the body and the massage head and said head includes application surface and two massage wheels located along two initial parallel longitudinal axes, which are separated and extend partially outside the application surface. The massage head includes to cause the two wheels to rotate in synchronization and in opposite directions so that, when seen in perpendicular plane to the two axes with the wheels toward the bottom, section of wheel located on the left which extends past the application surface turns counterclockwise and section of wheel located on the right which extends past the application surface turns clockwise. A wheel spacing adjustment system is designed to initially create a minimum distance between the wheels then to adjust the distance to reach a position of equilibrium.

14 Claims, 5 Drawing Sheets

(51) Int. Cl.
  *A61N 1/30* (2006.01)
  *A61N 1/04* (2006.01)
  *A61H 15/02* (2006.01)
  *A61H 23/02* (2006.01)
  *A61N 5/06* (2006.01)

(52) U.S. Cl.
  CPC ............... *A61H 2015/0014* (2013.01); *A61H 2015/0057* (2013.01); *A61H 2201/0188* (2013.01); *A61H 2201/10* (2013.01); *A61H 2201/105* (2013.01); *A61H 2201/1463* (2013.01); *A61H 2201/1685* (2013.01); *A61H 2205/022* (2013.01); *A61N 2005/0659* (2013.01); *A61N 2005/0663* (2013.01)

(56) References Cited

U.S. PATENT DOCUMENTS

| | | | | |
|---|---|---|---|---|
| 4,127,116 | A * | 11/1978 | Pannetier | A61H 15/0085 601/125 |
| 4,729,368 | A * | 3/1988 | Guitay | A61H 7/008 15/415.1 |
| 2003/0073937 | A1 * | 4/2003 | Guitay | A61H 7/008 601/6 |
| 2007/0173749 | A1 * | 7/2007 | Williams | A61H 7/00 601/123 |
| 2008/0306415 | A1 * | 12/2008 | Chan | A61H 15/0085 601/93 |
| 2010/0010401 | A1 * | 1/2010 | Tudico | A61H 7/005 601/118 |

* cited by examiner

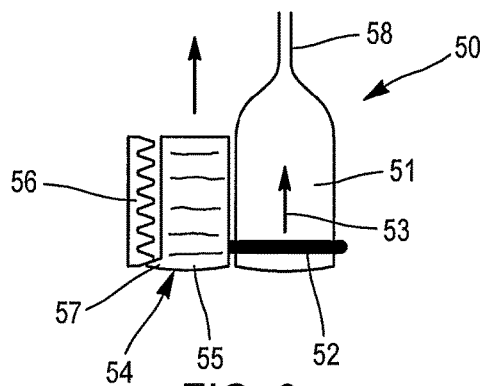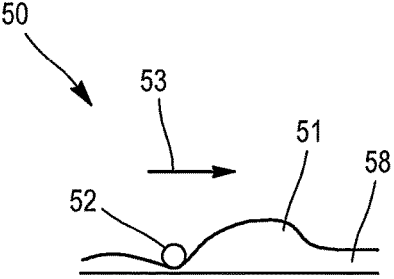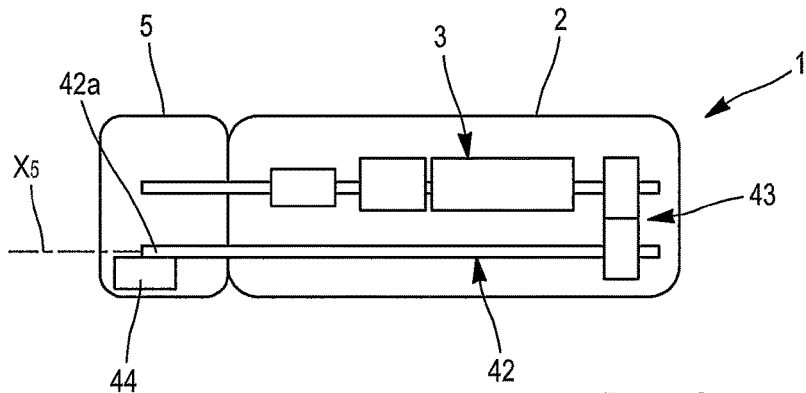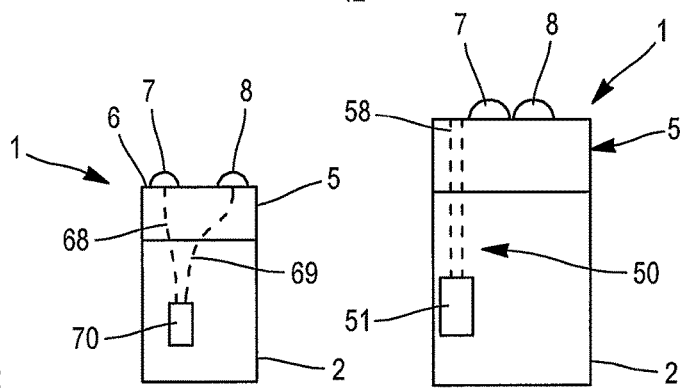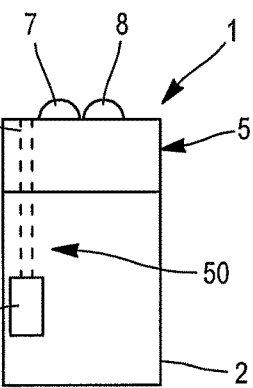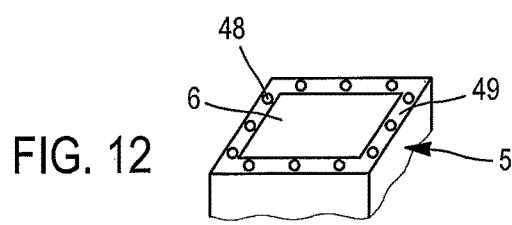
FIG. 6    FIG. 7    FIG. 8    FIG. 9    FIG. 10    FIG. 11    FIG. 12

MASSAGE DEVICE WITH A MASSAGE HEAD EQUIPPED WITH MASSAGE WHEELS

CROSS-REFERENCE TO RELATED APPLICATION

This application claims priority to French Patent Application No. 1261108 filed Nov. 22, 2012, the disclosure of which is hereby incorporated by reference in its entirety.

FIELD OF THE INVENTION

This invention concerns the domain of equipment for treating skin, in particular, on the face. The device in accordance with the invention allows, at a minimum, the skin to be massaged to improve its tone. A massage device in accordance with the invention may be used in households whose members wish to improve their appearance by changing, firming and rejuvenating their skin, in particular, on the face.

BACKGROUND OF THE INVENTION

Skin massage equipment generally consists of a body with a motor and a massage head which includes massage elements designed to be activated by the motor through a transmission mechanism. Current prior art in this domain is known in patents or patent filings EP 0 666 071 A1, FR 2 589 726 A1, and EP 1 973 510 B1.

In document EP 0 666 071 A1, the massage device includes two elements in the shape of a paddle which turn in opposite directions to move said paddles which pucker the skin. In one variation, this massage device includes an soft wired element which forms a ring where the two extremities rotate in opposite directions, allowing the ringed section to pucker the skin.

In document FR 2 589 726 A1, the massage device includes two wheels located on the application surface along two parallel axes a short distance from one another. A transmission mechanism causes the two wheels to rotate in the same direction. A mechanism to change the separation of the wheels is located on the device along with a recall mechanism to move the wheels apart. When the massage device is used, the wheels in the initial position are separate and rotate in the same direction; one of the wheels seeks to work with the other wheel due to the separation adjustment mechanism and the effect on said wheel which is in contact with the skin, while the recall mechanism tries to return said wheel to a position separated from the other.

In document EP 1 973 510 B1, the massage device includes two wheels located on the application surface along parallel axes with the wheels separated from one another. The massage device includes a mechanism to control the wheels located to allow the first wheel to rotate in one direction and block the rotation of the first wheel in the other direction and vice versa for the second wheel. Accordingly, when the massage device is applied to the skin and moved in one direction, only the first wheel rotates in one direction, which puckers the skin and vice versa when said massage device is moved in the other direction, only the second wheel rotates in the opposite direction, which puckers the skin.

The purpose of the invention is to design a massage device to optimize how the skin is worked by puckering it to work facial skin and muscles more thoroughly, pleasantly and effectively compared to massage equipment of the prior art, all while avoiding unpleasant sensations during the application of the massage device to the skin.

SUMMARY OF THE INVENTION

To this end, the invention concerns a massage device with a body which contains a motor and a massage head. Installation mechanisms are located between the body and the massage head. The head includes an application surface which is positioned parallel to the surface of the user's skin during use and two massage wheels which are located along two initial parallel longitudinal axes, with a gap between them, which partially extend beyond application surface. In accordance with the invention, the massage head includes a transmission mechanism designed to be driven by the motor to cause the two wheels to rotate in synchronization and in opposite directions so that, when seen in plane perpendicular to the two axes with the wheels toward the bottom, the section of the wheel on the left which extends past the application surface turns counterclockwise and the section of the wheel on the right which extends past the application surface rotates clockwise. Further, in accordance with the invention, the massage head includes a wheel spacing adjustment system which is triggered by the pressure placed on these wheels when they rotate which is designed to initially crate a minimum distance between the wheels and then to adjust the wheel spacing until an equilibrium of the pressure placed directly and/or indirectly on these wheels is reached. Accordingly, the characteristics of the massage device in accordance with the invention allow an initial position of the wheels to be determined with a minimum distance between them which, in combination with their opposite rotation as defined above, encourages the immediate, fortifying puckering of the skin when the massage device is applied, while the configuration of the adjustment system then allows the wheels to move apart under the pressure placed on the skin until an equilibrium is reached. This controls and limits the pinching efforts on the skin so that it is not painful, while adjusting to skin thickness, which varies depending on skin location, from person to person and user sensitivity.

The installation mechanism between the massage head and the body may be of various designs, from a massage head which is integrated completely with the body to a removable installation system between the massage head and the body.

In one preferred implementation of the massage device covered by the invention, the transmission mechanism includes two initial identical geared wheels which intermesh and which are located along second axes where said second axes are parallel to one another and to the two initial axes. One of said initial geared wheels is meshed with a motor to rotate. Further, this transmission mechanism includes two second identical geared wheels which mesh respectively with the two initial geared wheels where said second wheels are geared and located respectively along the first axes and driven by the wheels.

Of course, other variants of implementation of the transmission mechanism are possible. The gearing could be replaced by wheels or pulleys and belts placed to rotate the wheels in the desired direction.

In accordance with the massage device covered by the invention, the adjustment system includes a wheel support mechanism designed to allow wheel spacing to be increased or decreased depending on the pressure on said support mechanism in either direction.

In one preferred implementation of the massage device covered by the invention, the wheel support mechanism consists of two supports on which the wheels are respectively mounted using a pivot connection along the initial axes. Further, supports are shown respectively using a pivot connection on two shafts located respectively along the two second axes.

In accordance with the massage device covered by the invention, the adjustment system includes a recall mechanism designed to put pressure on the wheels to move them together below a skin resistance threshold when the massage device is applied. Beyond this threshold, the force of the springs is less than skin resistance and, therefore, the wheels separate.

In one preferred implementation of the massage device, these recall mechanism include springs located between the two supports or against the wall of the massage head to encourage the two wheels to move closer together.

In accordance with the massage device covered by the invention, it includes stops designed to limit the minimum distance between the two wheels when they are moved together by the recall mechanism. This limits the pressure on the skin when the massage device is initially applied.

The massage device covered by the invention includes a mechanism adjustment to adjust the position of the stops which is designed to modify the minimum distance between the wheels. That allows the massage device to be better adjusted depending on the user to prevent the puckering of the skin from becoming too intense when the massage device is initially applied.

In accordance with the massage device covered by the invention, the massage wheels are made of a material and in a shape designed to catch and work the skin without pain.

The massage device covered by the invention includes a wave emission system on the application surface. These waves may be electromagnetic waves, in particular light, visible or in the infrared range, or sonic, e.g., ultrasound. This also allows the user's skin to be worked in an additional manner.

In a planned example of implementation, these waves consist of red or orange light. The massage device covered by the invention includes a cosmetic product distribution system designed to distribute said cosmetic product on the massage wheels and/or directly on the user's skin. Depending on the configuration of the distribution system, the cosmetic product may be distributed naturally, manually and/or automatically.

That allows the skin to be treated using cosmetic products in additional to the wheels.

The massage device covered by the invention includes a vibration system designed to vibrate the massage head or only the wheels.

That further allows the skin to be worked and relaxed (a sensation of well-being) by applying light pressure on the skin in addition to the puckering by the wheels.

In accordance with the massage device covered by the invention, the installation mechanism between the body and the massage head is designed to connect, in a removable manner, the massage head to the body. This allows the massage head to be easily removed to be replaced by identical or different massage head.

The massage device covered by the invention includes a trans-dermal ionization treatment mechanism which is configured to transfer an electric current to the skin during the application of said massage device to increase and/or accelerate penetration of a cosmetic product which may either be distributed by the cosmetic product distribution system described above or applied directly to the skin by the user. Ionization is a process which was initially developed for the application of drugs to the skin, in particular for sports medicine, but is also appropriate to best insure penetration of cosmetic products. In one implementation, this trans-dermal ionization treatment mechanism includes two electrodes with different electrical potentials which may be installed on the massage nozzles or wheels and/or on the application surface of the massage head. The settings of the massage device in accordance with the invention allow, in particular when it also includes a products cosmetic distribution system, trans-dermal ionization treatment prior to and/or during the application of the cosmetic product.

BRIEF DESCRIPTION OF THE DRAWINGS

The following description highlights the characteristics and benefits of the massage device in accordance with the invention, which relies on diagrams, including:

FIGS. 6 and 7 diagram a cosmetic product distribution system on the massage device;

FIG. 8 diagrams a vibration system on the massage device;

FIG. 9 diagrams a removable installation mechanism between the massage head and the body;

FIG. 10 diagrams a trans-dermal ionization treatment mechanism on the massage device;

FIG. 11 diagrams a cosmetic product distribution system on the massage device;

FIG. 12 diagrams a wave emission system on the massage device;

DESCRIPTION OF THE INVENTION

Figure 1:
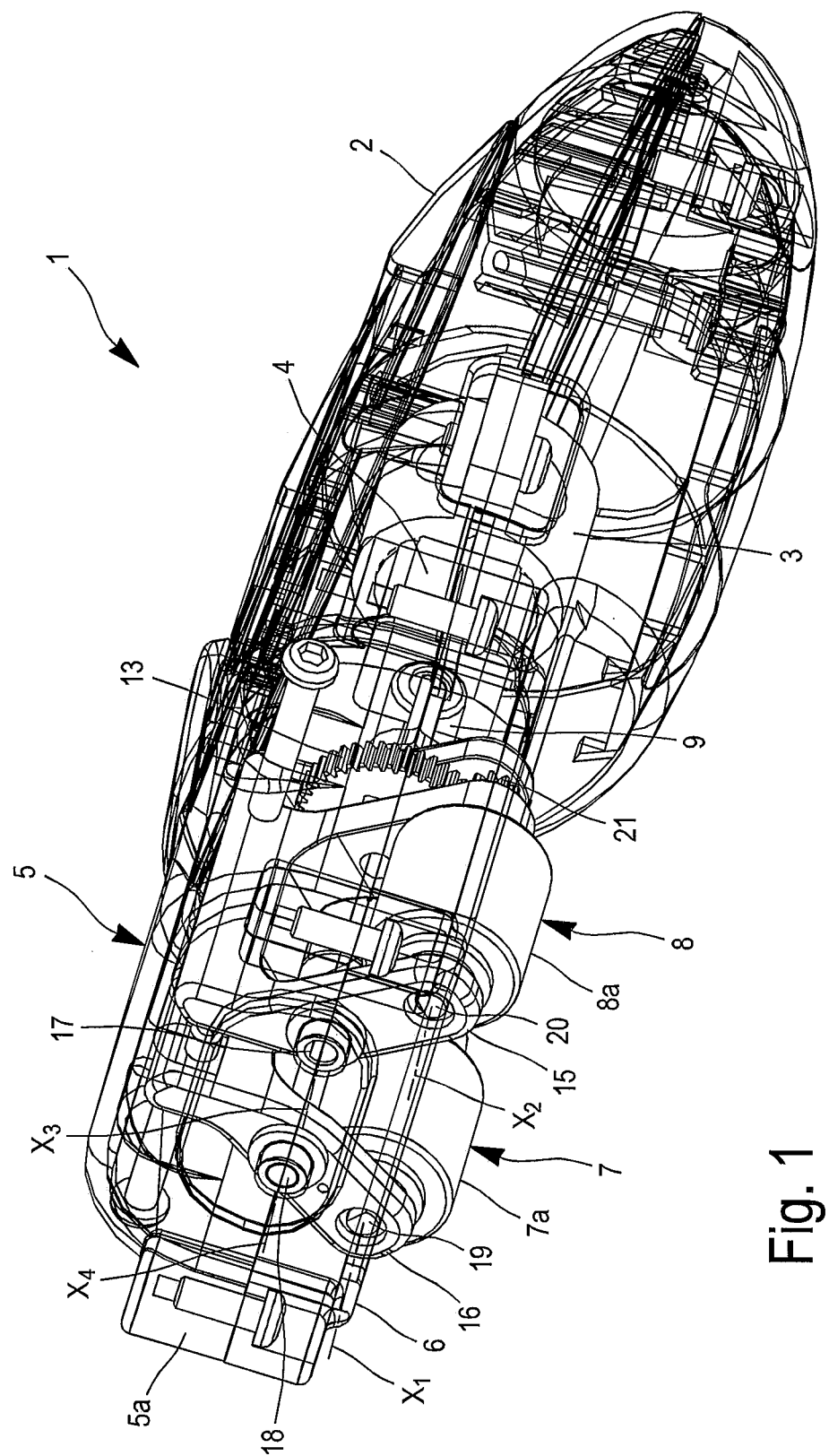
FIG. 1 is a side view of one implementation of the massage device in accordance with the invention.
Figure 2:
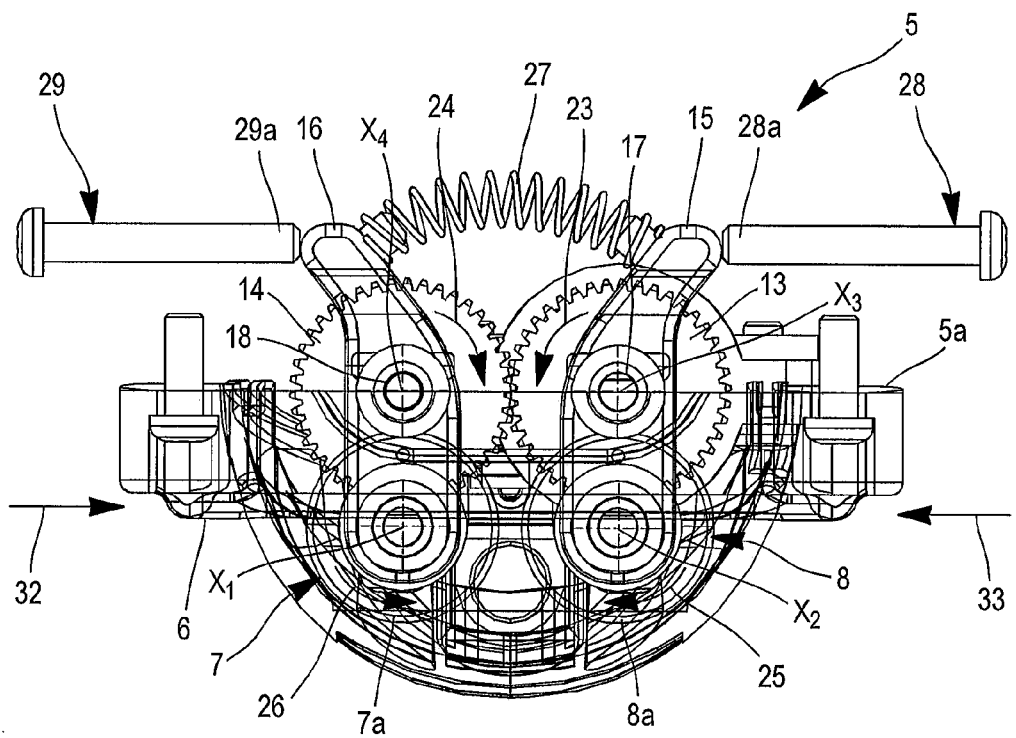
FIGS. 2 and 3 show two different positions of the massage wheels.

As shown in FIGS. 1 and 2, massage device 1 includes body 2 within which is located motor 3 which is electrically powered by a connection either to an external electrical source (an electrical outlet and low voltage transformer), or to an internal electrical source (rechargeable or disposable batteries). Massage device 1 also includes reduction gear 4 located on the output of motor 3 to reduce its rotation speed and adjust it to the type of use. Massage device 1 includes also massage head 5. Body 2 and massage head 5 are constructed out of a single milled piece. However, in one implementation variation, there could be two separate removable pieces.

As shown in FIGS. 1 to 5, the massage head includes application surface 6 and two massage wheels 7 and 8 of which section 7a and 8a extend beyond application surface 6. These wheels 7 and 8 are located on two parallel axes X1 and X2. In accordance with this implementation, motor 4 includes drive train 9 which includes flat section 10 which is engaged in hole 11 located on shaft 12. This shaft 12 is driven by geared wheel 13. Therefore, motor 3 rotates geared wheel 13 along axis X3. This geared wheel 13 meshes with another identical geared wheel 14 which is located on axis X4.

As shown in FIGS. 1 to 5, massage head 1 includes two supports 15 and 16. These supports 15 and 16 are shown using a pivot connection along axes X3 and X4, respectively, using two shafts 17 and 18. Using pivot connections along axes X1 and X2, these supports accept wheels 7 and 8 using two shafts 19 and 20 mounted using a pivot connection on said supports 15 and 16.

Figure 3:
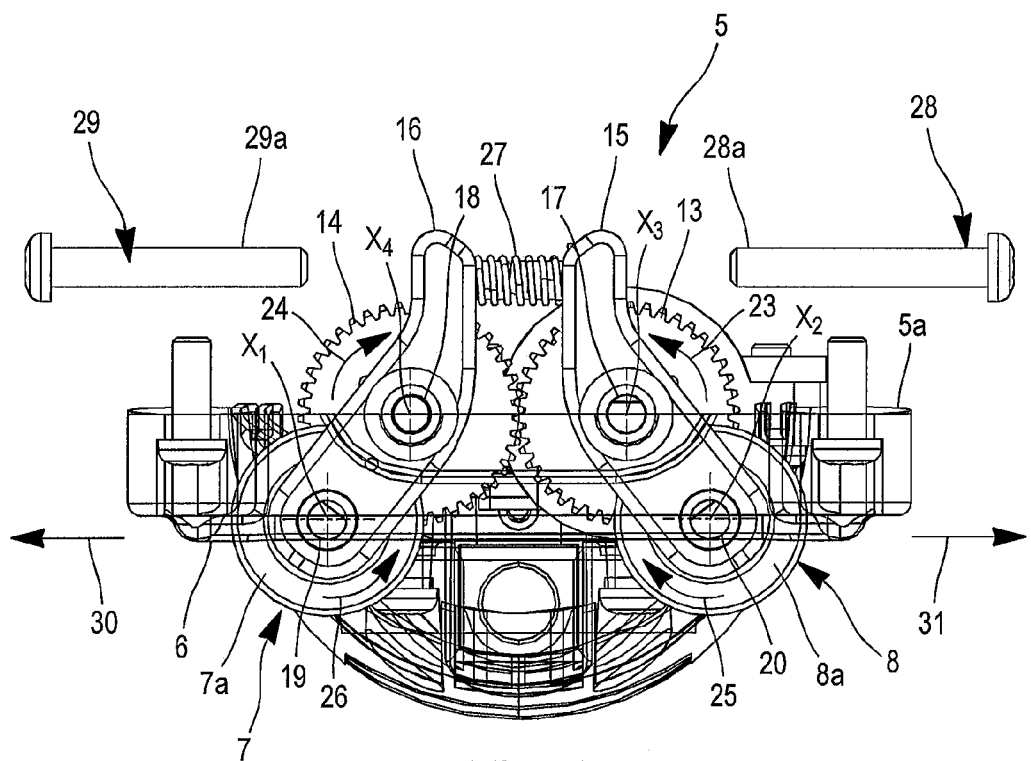

As shown in FIGS. 1 and 3, the massage head includes two other identical geared wheels 21 and 22. Geared wheel 21 is driven by wheel 8 through shaft 20 using, for example, flutings (not shown) located between these elements. Similarly, geared wheel 22 is driven by wheel 7 through shaft 19. Geared wheel 21 meshes with geared wheel 13. Similarly, geared wheel 22 meshes with geared wheel 14.

Accordingly, when geared wheel 13 is driven by motor 3, which turns in the direction of arrow 23, geared wheel 14 turns in the direction of arrow 24, which allows geared wheel 21 to turn in the direction of arrow 25 and geared wheel 22 to turn in the direction of arrow 26. Accordingly, wheel 7 is driven in the direction of arrow 26 and wheel 8 in the direction of arrow 25.

Figure 4:
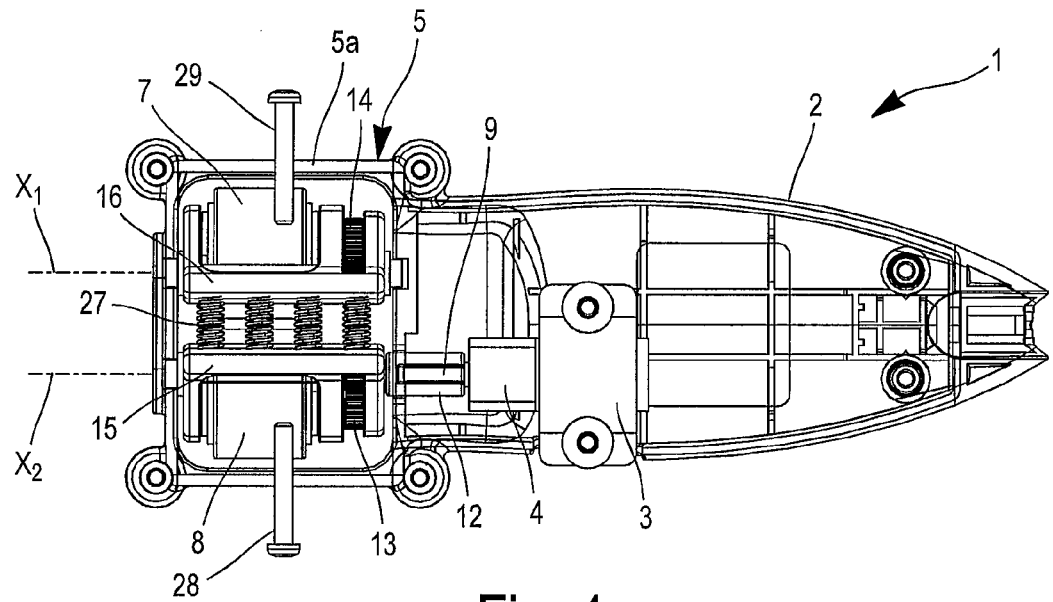
FIG. 4 shows the massage device of FIG. 1 from above and the side.
Figure 5:
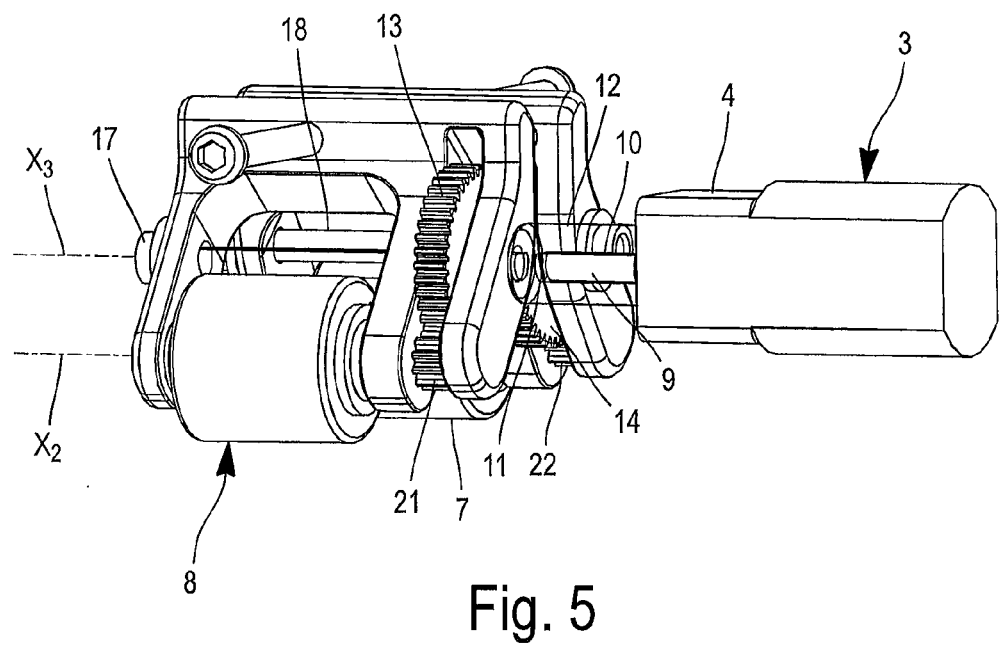
FIG. 5 shows the transmission mechanism of FIG. 1.

As shown in FIGS. 2 to 4, springs 27 are located between two supports 15 and 16. In the initial position, these springs 27 press against supports 15 and 16 and hold them in position against extremities 28a and 29a with two adjustment screws 28 and 29 located on massage head 5. Accordingly wheels 7 or 8 are separated from one another at a minimum distance in their initial position. Further, adjustment of screws 28 and 29 allows the minimum distance between these two wheels 7 and 8 to be modified.

When sections 7a and 8a of wheels 7 and 8 are applied to the skin, the opposite rotation directions of wheels 7 and 8 in the direction of arrows 26 and 27 puckers the skin. The pressure of the skin on these wheels when this pressure exceeds that of springs 27 allows these springs 27 to be compressed and moves the wheels in the direction of arrows 30 and 31 shown in FIG. 3. On the other hand, if the pressure of the skin on wheels 7 and 8 is less than the pressure of springs 27, these springs 27 separate and move wheels 7 and 8 in the direction of arrows 32 and 33 as shown in FIG. 2, until a position of equilibrium is reached.

Variants of the implementation of the transmission mechanisms on massage head 5, which work based on the same principle, are possible without falling outside the scope of the invention. In particular, the springs could be located between supports 15 and 16 and casing 5a of massage head 5 in which the transmission mechanism is located. These springs extend to move wheels 7 and 8 to an initial position with a minimum distance.

Figure 13:
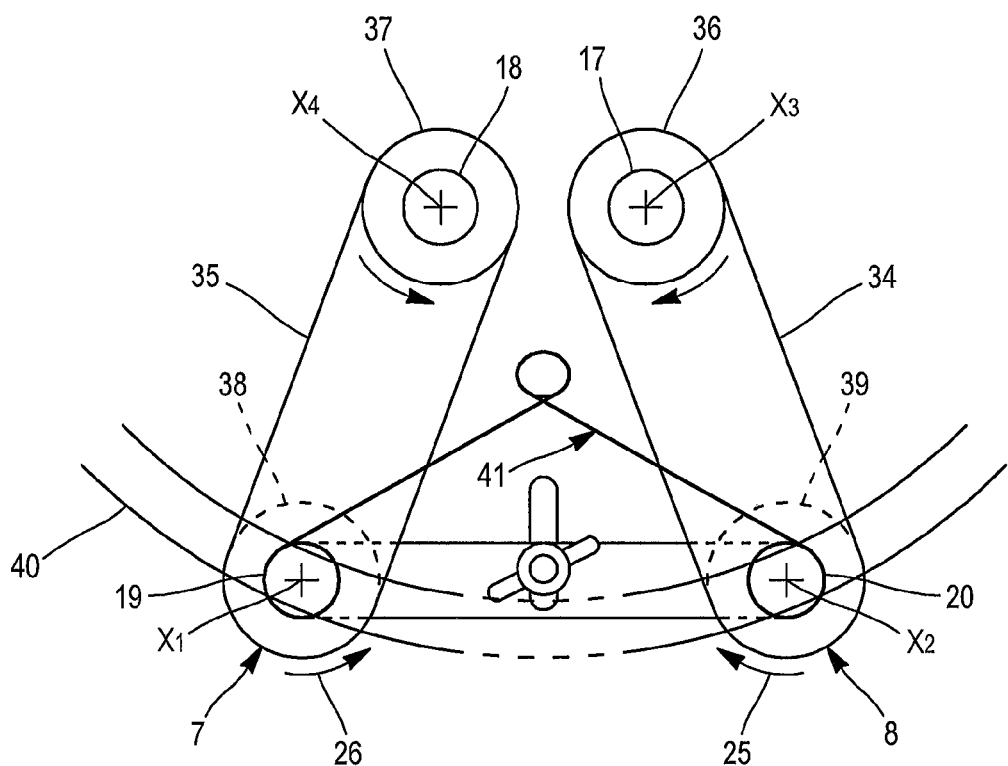
FIG. 13 shows a variation of implementation of a transmission mechanism on a massage head.

As shown in FIG. 13, wheels 7 and 8 could also be driven by belt mechanism 34 and 35 and pulleys 36, 37, 38 and 39 driven by motor 3 to replace wheels geared 13, 14, 21 and 22, which mesh with them. Similarly supports 15 and 16 could be replaced by guide system 40 of shafts 19 and 20 driven by wheels 7 and 8. Recall spring 41 is also located between shafts 19 and 20 to move the wheels to a minimum distance.

Other characteristics are possible on massage device 1 covered by the invention.

As shown in FIG. 8, massage device 1 includes shaft 42 which is rotated in the direction of axis X5 by motor 3 using gearing system 43, which known to those familiar with the art. Extremity 42a of this shaft 42 is located within massage head 5, for example, on casing 5a or supports 15 and 16 and accepts counter equilibrium 44 which turns irregularly around axis X5 and vibrates massage head 5 when massage device 1 is applied. Other vibration system variants are possible.

In particular, only wheels 7 and 8 could vibrate.

Figure 14A:
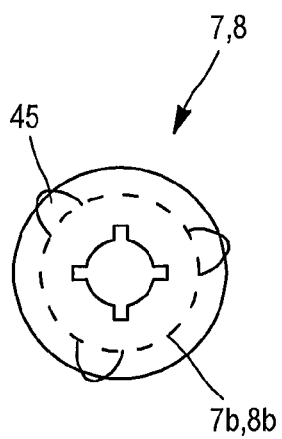
FIGS. 14A-14C show various wheel shapes.
Figure 14B:
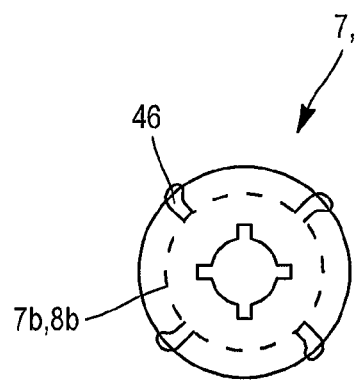
Figure 14C:
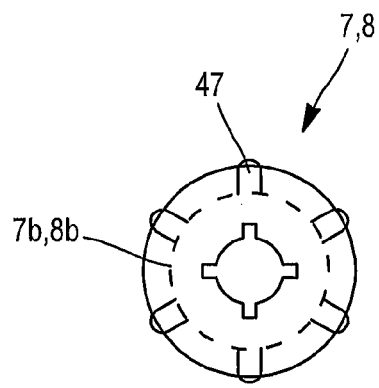

As shown in FIGS. 14A-14C, external section 7b and 8b of massage wheels 7 and 8 may take different shapes, e.g., fold 45 in FIG. 14A, hook 46 in FIG. 14B and sprocket 47 in FIG. 14C. Other forms are possible. Further, massage wheels 7 and 8 are made of a material such as elastomere which, in combination with these shapes, better catches the skin when massage device 1 is applied.

In one variation shown in FIG. 12, massage device 1 includes luminescent diodes 48 which are controlled by an electronic box (not shown) located within body 2 on application surface 6 on massage head 5. These luminescent diodes 48 may be lit either automatically when massage head 5 is activated or individually using a separate control button (not shown). Luminescent diodes 48 could, for example, be located on peripheral edge 49 of application surface 186 or even distributed on said application surface 6 outside the range of motion of massage wheels 7 and 8. Various colors of luminescent diodes could be used, depending on the wave length and/or treatment desired, or even a control box to change the wave length of these luminescent diodes 48.

In one variation shown in FIGS. 6, 7 and 11, massage device 1 includes cosmetic product distribution system 50 which includes flexible product reservoir 51 on which barrette 52 pushes, which moves in the direction of arrow 53 along product reservoir 205. A trigger system 54 moves barrette 52 in the direction of 53. This trigger system 54 could, for example, consisting of button 55 which is part of barrette 52 which moves in the direction of this arrow 53 when manually triggered. Notched piece 56 holds notch 57 onto button 55 each time it is pressed to hold barrette 52 in position as it advances toward product reservoir 51. Distribution system 50 includes tube 58 the location of which allows the cosmetic product to be distributed on application surface 6, either between wheels 7 and 8 or through wheels 7 and 8, as shown in FIG. 11. Other variants of the cosmetic product distribution system are possible.

In particular, an automatic triggering system could allow the cosmetic product to be distributed continuously and evenly using, for example, a pump. A natural cosmetic product distribution system could also be used where the cosmetic product is distributed evenly using physical phenomena which do not require external action.

As shown in FIG. 9, variants in massage head 5 can be quickly installed and removed from body 2 could be envisioned. This would allow massage head 5 to be easily changed. In this regard, removable fixation system 59 between massage head 5 and body 2 could be envisioned. For example, as shown in FIG. 12, body 2 could include notches 60 and 61 and massage head 5 include piece 62, which accepts transmission mechanism 63 which moves massage wheels 7 and 8 is connected the shaft 9 of motor 3. This piece 62 includes notches 64 and 65 of retraction mechanism 66 and 67 of notches 219 and 220 which allows them to be move into notches 60 and 61 and to also remove them from these notches 60 and 61.

In one implementation variation shown in FIG. 10, massage device 1 includes two electrodes 68 and 69 which have different electrical potential.

These electrodes 68 and 69 could be located on massage wheels 7 and 8 or on application surface 6. These electrodes 68 and 69 are powered by electrical source 70 located in body 2. This design allows trans-dermal ionization treatment prior to or during the application of a cosmetic product on the skin, which allows of accelerate the penetration of the cosmetic product. This cosmetic product may be distributed naturally, manually or automatically by massage device 1, or even applied directly on the skin by the user.

These additional aforementioned characteristics of the different implementation variants of massage device 1 could be implemented in combination with either transmission mechanisms on the massage head as described above, or even with other variants possible within the scope of the invention.

The invention claimed is:

1. A massage device (1) including a body (2) which contains a motor (3) and a massage head (5), with an installation mechanism (59) located between the body and the massage head; said head includes an application surface (6) and two massage wheels (7 and 8) located along two initial parallel longitudinal axes (X1 and X2), which are separated and extend partially beyond the application surface, where the massage head includes, first, a transmission mechanism designed to be driven by the motor to cause the synchronized and inverse rotation of the two massage wheels so that, when seen in a plane perpendicular to the two initial axes with the two massage wheels at the bottom, a section (7a) of the massage wheel (7) located on the left which extends beyond the application surface, turns counterclockwise and a section (8a) of the massage wheel (8) located on the right which extends outside the application surface, turns clockwise and, in addition, a wheel spacing adjustment system based on the pressure placed on the massage wheels when they rotate is designed to initially create a minimum distance between the massage wheels and then to adjust the distance between them until a position of equilibrium of the pressure on the massage wheels is reached.

2. The massage device (1) in accordance with claim 1 in which the transmission mechanism includes:
   two initial identical geared wheels (13 and 14) which intermesh and are located along second axes (X3 and X4) which are parallel to one another and to the two initial axes (X1 and X2), and said initial geared wheels (13) are rotated by the motor (3) and,
   two second identical geared wheels (21 and 22) which mesh with the two initial geared wheels and said second geared wheels are located respectively along with the initial axes and driven by the massage wheels (7 and 8).

3. The massage device (1) in accordance with claim 2 in which the adjustment system includes a support mechanism (15 and 16) of the massage wheels (7 and 8) designed to increase or decrease the wheel spacing based on the pressure on said support mechanism in one direction or the other.

4. The massage device (1) in accordance with claim 3 in which the support mechanism of the massage wheels (7 and 8) includes two supports (15 and 16) on which the massage wheels are respectively mounted using a pivot connection along the initial axes (X1 and X2) and said supports are disposed respectively using a pivot connection on two shafts (17 and 18) located along the two second axes (X3 and X4).

5. The massage device (1) in accordance with claim 1 in which the adjustment system includes a recall mechanism (27 and 41) designed to put pressure on the massage wheels (7 and 8) to move them together below a resistance threshold.

6. The massage device (1) in accordance with claim 5 in which the recall mechanism includes springs (27 and 41) designed to move the two massage wheels (7 and 8) closer together.

7. The massage device (1) in accordance with claim 5 which includes stops (28a and 29a) designed to limit the minimum distance between the two massage wheels (7 and 8) when they are moved together by the recall mechanism.

8. The massage device (1) in accordance with claim 7 which includes an adjustment mechanism (28 and 29) of the position of the stops designed to modify the minimum distance between the massage wheels (7 and 8).

9. The massage device (1) in accordance with claim 1 in which the massage wheels (7 and 8) are in form (45, 46 and 47) and substance designed to catch and work a user's skin without pain.

10. The massage device (1) in accordance with claim 1 which includes a wave emission system (48) on the application surface (6).

11. The massage device (1) in accordance with claim 1 which includes a distribution system (50) of a cosmetic product designed to distribute said cosmetic product on the massage wheels (7 and 8) and/or directly on a user's skin.

12. The massage device (1) in accordance with claim 1 which includes a vibration system (42 and 44) designed to vibrate the massage head (5) or the massage wheels.

13. The massage device (1) in accordance with claim 1 in which the installation mechanism (59) between the body (2) and the massage head (5) is designed to connect, in a removable manner, the massage head on the body.

14. The massage device (1) in accordance with claim 1 which includes a trans-dermal ionization treatment mechanism (68, 69 and 70) which is designed to transfer an electric current to a user's skin during the application of said massage device to increase and/or accelerate penetration of a cosmetic product.

* * * * *